United States Patent [19]
Clarke et al.

[11] 3,947,336
[45] Mar. 30, 1976

[54] HALOGENATION OF HETEROCYCLIC COMPOUNDS

[75] Inventors: James A. Clarke, Cottingham; Otto Meth-Cohn, Salford, both of England

[73] Assignee: Synthetic Chemicals Limited, Four Ashes, near Wolverhampton, England

[22] Filed: Feb. 21, 1975

[21] Appl. No.: 551,525

[30] Foreign Application Priority Data
Feb. 28, 1974 United Kingdom.............. 9116/74

[52] U.S. Cl. ......................................... 204/158 HA
[51] Int. Cl.² .......................................... B01J 1/10
[58] Field of Search ............................ 204/158 HA

[56] References Cited
UNITED STATES PATENTS
3,190,825   6/1965   Huyser........................ 204/158 HA

*Primary Examiner*—Howard S. Williams
*Attorney, Agent, or Firm*—Ryder, McAulay, Fields, Fisher & Goldstein

[57] ABSTRACT

A process is described for making thiophens and furans substituted by bromo aliphatic or alaromatic groups by brominating the corresponding aliphatic or alaromatic substituted thiophen or furan by a process comprising gradually adding bromine to an organic liquid phase containing the thiophen or furan in the presence of a radical initiator and illumination.

17 Claims, No Drawings

HALOGENATION OF HETEROCYCLIC COMPOUNDS

This invention relates to the production of furans and thiophens of Formula 1

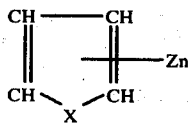

where $n$ is 1 or 2, Z is $CBrR_2$ where the radicals R may be the same or different and are bromine, hydrogen or an aliphatic (for example alkyl) or aromatic (for example phenyl) group, and X is oxygen or sulphur. When $n$ is 2 the groups Z can be the same or different. In these heterocycles the ring may contain additional substituents provided that at least one CH group in the ring is unsubstituted. Adjacent positions on the ring may be substituted by a fused ring. Polycyclic compounds of formula 1 include benzofurans and, especially, benzothiophens.

There is increasing demand for 5-membered heterocycles for various purposes, particularly as intermediates in the synthesis of pharmaceutically useful and other organic compounds. (See e.g. N. R. Clark, Manufacturing Chemist and Aerosol News, pp. 3–7, July 1972). To permit this further reaction it is generally desirable to have a methyl or other alkyl or alkaryl group substituted into the ring to provide an alpha carbon atom on which further reaction can be conducted. For example it is often necessary to form a heterocycle having a group such as a carboxylic or aldehyde group substituted into the ring. The provision of compounds of Formula 1 is therefore very desirable since, by virtue of the halogen atom or atoms in the group Z there is a reactive position in the carbon atom adjacent the ring. In particular such compounds where Z contains 2 halogen atoms would be very desirable as they would greatly simplify the subsequent synthesis of, for example, the aldehyde derivatives.

Most work relating to the formation of compounds of Formula 1 appears to have been conducted on the thiophens. It is known that thiophen can be halomethylated using, for example, formaldehyde and hydrochloric acid onto the 2 position. This reaction is acceptable if 2-chloromethyl thiophen is desired but it will not give the 3-substituted compound unless both the 2 and the 5 positions are blocked by some other group. Also the reaction is incapable of producing the dihalo compound.

Most of the work relating to the production of compounds of Formula 1 has therefore concentrated on the halogenation of, for instance, alkyl thiophens and furans, including substituted derivatives thereof, for instance alkyl benzothiophen. In particular, most of the work has been on monomethyl thiophens.

Vapour phase bromination of 2-methyl thiophen to convert the $CH_3$ group into the group $CH_2Br$ has been reported at JACS 1953, 75, pages 3517–3520. However the use of vapour phase conditions, for example a temperature of 400°C, may be inconvenient, the process has only been reported as being conducted on 2-methyl thiophen, and only gives the monobromo derivative.

It would of course be much more convenient to conduct the halogenation in the liquid phase and it might be thought that conditions similar to those for the halogenation of toluene, for example reaction with bromine under conventional moderate free radical generating conditions, for example direct sunlight, would be satisfactory. However it has long been known that these conditions do not give chain substitution but instead almost exclusively give nuclear substitution by the halogen atoms. For example reference can be made to Opolski: Bull. Internat. de L'Academie des Sciences de Cracovie, 1904, 727–732 and Steinkopf: Ann. 1934, 513, 281–294. Because of this known complete failure of liquid phase direct halogenation to give chain substitution, as opposed to nuclear substitution, it appears that all research in this field has been concentrated on methods of indirect halogenation, for example using N-bromosuccinimide. These of course suffer from the inherent disadvantage that they require the initial costly step of forming the brominating agent from bromine. The process is generally conducted either in the presence of a radical initiator or light. A suitable process for the production of 3-bromomethyl thiophen is described in Campaigne and Tyllar: Org. Syn. 33, 96–98 while a process for the halogenation of 3-methyl benzothiophen is described in Brabander: J. Heterocyclic Chem. 1973, 10, 127–129.

Even with indirect halogenation there is still a tendency for nuclear substitution to occur although the tendency does depend upon what other substituents there are in the ring. Probably because of this except when the ring has been fully substituted or greatly deactivated (for example by the provision of a nitro substituent) it has been impossible to form the dihalo derivatives (Z in Formula 1 containing two halogens). Thus it has not been possible to make the dihalo derivative of, for example, 2- or 3-methyl thiophen except accompanied by excessive nuclear halogenation. This is a great disadvantage because the dihalo derivatives would be expected to be greatly preferred to the monohalo derivatives for use in subsequent syntheses, for example to the aldehyde. Indirect halogenation in the known manner has the disadvantage that it tends to give very variable and unreliable results (see JCS 1952 5044–5046).

Thus we believe the state of the art at present is that except for a few particular substituted compounds there is no satisfactory known way of making the dihalo compounds of Formula 1 (Z contains two halogens) from compounds such as alkyl thiophens, despite the obvious desirability of these compounds, halomethylation has been described only as providing the 2-monohalomethyl thiophen, it is known to be impossible to halogenate directly in the liquid phase compounds such as alkyl thiophens without nuclear halogenation occurring almost exclusively and that it is known that the monohalo compounds of Formula 1 can be made by indirect halogenation which itself is inconvenient and rather unreliable. Also there appears to be no known way of making tribromo compounds (Z contains three bromines).

Our object has been to devise a process of making compounds of Formula 1 from readily available compounds (such as alkyl thiophens) by direct halogenation in the liquid phase, and in particular to devise a process that can also be operated to give the dihalo compounds of Formula 1, with little substitution of halogen into the ring, and that preferably can also be operated to yield trihalo compounds of Formula 1.

According to the invention we make a compound of Formula 1

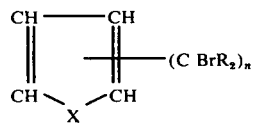

from a compound of Formula 2

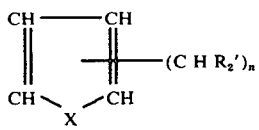

in which n is 1 or 2, X is oxygen or sulphur, the radicals R and R' may be the same or different and are Br, hydrogen or an aliphatic or aromatic groups, and in which each ring may contain additional substituents provided that at least one CH group is unsubstituted, by a process comprising gradually adding bromine to an organic liquid phase containing the compound of Formula 2 and reacting the bromine with the compound in the organic liquid phase in the presence of a radical initiator and illumination by visible or ultra violet light, the rate of addition of bromine being such that the liquid phase substantially never acquires a red brown colour.

It is particularly surprising that such a simple process is successful in view of the considerable amount of prior art that exists (and which is discussed above) and in view of the fact that when we carry out the process using chlorine instead of bromine we obtain, almost exclusively, ring halogenation.

The compound of Formula 2 used in the process is preferably a thiophen. Preferably n is 1. The or each group $CHR_2'$ preferably represents an alkyl or aralkyl group in which the carbon atom adjacent the ring carries at least one and preferably two hydrogen atoms. Thus typical values are methyl, ethyl and isopropyl or any other alkyl group having an alpha carbon atom carrying a hydrogen atom, the total number of carbon atoms in the alkyl group usually being less than 8, preferably not more than 4. A typical aralkyl group is benzyl. The alkyl or aralkyl group may additionally be substituted by groups that assist or at least do not hinder the reaction.

A compound in which either or both radicals R' are bromine can be brominated further by the process of the invention to produce a compound in which either or both radicals R are bromine. In fact this process probably occurs automatically during any process of the invention that yields a compound of Formula 1 where either or both radicals R are bromine. Generally it is preferred that no more than one radical R is bromine.

The thiophen or furan of Formulae 1 and 2 may contain additional substituents provided that at least one position in the ring is unsubstituted. There may be, for instance, one or two substituents. Preferred substituents are nitro, carboxylic, bromo, chloro, trifluoromethyl and alkyl. Additionally adjacent carbon atoms in the heterocyclic ring may be linked together through a carbocyclic or heterocyclic chain to form a fused ring system. Normally this fused ring is a benzene ring and preferably is on the 2,3-position. For example the thiophen may be a benzothiophen.

It is possible to use excess compound of Formula 2 to form the organic liquid phase but generally it is more satisfactory to use a different, inert, solvent. Any organic solvent can be used in the reaction provided that it can be put under reflux at a temperature at which the compounds of Formula 1 and 2 are sufficiently stable and provided it does not interfere with the reaction. Thus it must be inert in the sense that it is not halogenated during the reaction. Preferred solvents are carbon tetrachloride, chloroform, and benzene but other suitable inert solvents may be used.

The reaction should be conducted under reflux since the refluxing appears to assist the formation of products of Formula 1, remove the hydrogen bromide that is formed in the reaction, and reduce the tendency for nuclear bromination to occur. The reflux is preferably conducted under atmospheric pressure but if the combination of optimum reaction temperature and solvent requires it the reflux can be under reduced or elevated pressure. For example reduced pressure may be convenient when the reaction is conducted in the presence of excess of the compound of Formula 2. The reaction temperature is normally between 50° and 200°C, preferably between 70° and 110°C. Temperatures below 70°C tend to result in very low rates of reaction while instability of the compounds of Formulae 1 and/or 2 tends to become a problem with increasing temperature above 100°C or 110°C. The organic phase is preferably under reflux throughout the entire process, i.e. both during the addition of bromine and during any further period during which reaction occurs.

Any conventional radical initiator can be used. Peroxides, for instance benzoyl peroxide, and AZDN (azodiisobutyronitrile) are suitable, AZDN being preferred.

It is necessary that during the process the reaction mixture substantially never, and preferably never acquires the red brown colour characteristic of the presence of excess bromine. Instead the mixture should substantially never acquire a colour darker than orange and preferably it never acquires a colour darker than that of a ripe lemon. Accordingly the bromine must be added, usually with stirring, at a rate that is sufficiently slow so that there is no excess bromine in the liquid phase.

The rate of addition that can be used will depend upon the intensity of illumination, since increasing illumination will cause increasing rate of reaction and will thus permit increasing rate of addition of bromine. It is thus preferred to use strong illumination by visible or ultra violet light. Although it is possible that a part only of the visible spectrum is necessary for the illumination it is generally convenient to illuminate with white light. However light of a narrower wavelength band, particularly at the shorter end of the visible spectrum, may be used. By saying that the illumination is strong we mean that it is greater, and generally very much greater, than the illumination obtainable when exposing the reaction system to direct sunlight. The strong illumination can be achieved by focusing sunlight but more usually it is provided by a lamp, for example a tungsten lamp. On the small scale at least the lamp can be used to provide the reflux temperature but if necessary or desired separate heating means can be used to provide the temperature.

Conveniently the bromine is added dissolved in at least some of the solvent. The initiator can be added with the bromine or may be incorporated in the vessel separately.

The reaction results in the liberation of hydrogen bromide and it is necessary to remove this to prevent decomposition and nuclear halogenation occurring. In many instances the distillation under reflux achieves this removal, hydrobromic acid vapour being distilled off from the top of the reflux condenser. However, if in any particular process this is not sufficient or if the reaction is not under reflux then a hydrogen bromide acceptor may be included in the reaction mixture.

The total amount of bromine added controls the amount of bromination of the chain. When the amount is up to 1 mole per mole of compound of Formula 2 the product usually consists predominantly of the monobromo compound but to achieve optimum yield of this slightly in excess of 1 mole, for example 1 to 1.5 or 2 moles, bromine is preferably used and this gives increasing amounts of the dibromo compound. To obtain the optimum yield of dibromo compound preferably from 2 to 3 moles, for example 2.5 moles, bromine are added.

The monobromo compounds of Formula 1 are preferably separated from the reaction mixture by vacuum distillation, any dibromo compound being left in the distillation residue. Generally the most convenient way of utilising the dibromo compound is to react it in situ to a more stable compound, for example by hydrolysing it with water or aqueous sodium carbonate to the aldehyde, and then to separate the aldehyde from the reaction mixture. The dibromo compound can, alternatively, be distilled under reduced pressure.

The following are Examples of the invention. In all these the colour of the reaction mixture substantially never exceeded orange. In particular the mixture substantially never exceeded orange. In particular the mixture substantially never acquired the red brown colour characteristic of excess bromine. If it had, addition would have been stopped until the colour disappeared and, provided the colour went quickly, the reaction would then have been continued. The fact that the colour is present for a short while is not necessarily fatal to success but results do deteriorate sharply with increase in total time that the colour is present.

EXAMPLE 1

A 500 ml. 3-necked flask was fitted with a condenser, stirrer and dropping funnel, the outlet of which was below the surface of the carbon tetrachloride solvent (150 ml) and heated and lit by a 150 w. spotlight bulb.

AZDN (0.5g) dissolved in 3-methyl thiophen (20 g) was added down the reflux condenser. Immediately bromine was added (as a 25% solution by volume in CCl$_4$) drop by drop. The refluxing reaction mixture was kept a light yellow as 1.10 molar equivalents of bromine were added. The addition took 2 hours.

After all bromine had been added, stirring and illumination were continued for a further one-half hour. Analysis of the resulting reaction products by nuclear magnetic resonance spectroscopy gave the following molar percentages of thiophen compounds:

| 3-Methyl thiophen | 11% |
| 3-Thenyl bromide | 60% |
| 3-Thenylidine dibromide | 18.5% |

-continued

| 2-Bromo-3-methyl thiophen | 7.5% |
| 2-Bromo-3-Thenyl bromide | 3% |

This corresponds to a yield of 3-thenyl bromide of 67% based on the 3-methyl thiophen consumed.

EXAMPLE 2

The same procedure was used as in Example 1 except that 1.35 molar equivalents of bromine were added and the addition took 1½ hours.

After all bromine had been added, stirring and illumination were continued for a further one-half hour. Analysis of the resulting reaction products by nuclear magnetic resonance spectroscopy gave the following molar percentages of thiophen compounds:

| 3-Methyl thiophen | 31% |
| 3-Thenyl bromide | 40% |
| 2-Bromo-3-methyl thiophen | 6% |
| 2-Bromo-3-thenyl bromide | 18% |

This corresponds to a yield of 3-thenyl bromide of 58% based on the 3-methyl thiophen consumed.

The solvent was removed under vacuum and vacuum distillation of the remaining oil gave 14.4 g. 3-thenyl bromide and 9.9g 2-bromo-3-thenyl bromide, weights which are in close agreement with the NMR analysis of the reaction products.

EXAMPLE 3

In apparatus as above 2.5 molar equivalents of bromine were added to 3-methyl thiophen (20 g) in CCl$_4$. The addition took about 3 hours and after completion, heating and illumination was continued for one-half hour. Analysis of the resulting reaction products by nuclear magnetic resonance spectroscopy gave the following molar percentages of thiophen compounds:

| 3-Methyl thiophen | 3% |
| 3-Thenyl bromide | 28% |
| 3-Thenylidine dibromide | 29% |
| 2-Bromo-3-methyl thiophen | 2% |
| 2-Bromo-3-thenyl bromide | 18% |
| 2-Bromo-3-thenylidine dibromide | 17% |

The solvent was removed under vacuum and the reaction mixture was hydrolysed with aqueous sodium carbonate solution. After steam distillation, separation, and distillation, 7.1 g of thiophen-3-aldehyde were obtained. This was in good agreement with the N.M.R. analysis.

EXAMPLE 4

In apparatus as in Example 1 but with some additional illumination from a 100 watt tungsten filament lamp at the side of the flask, 2.5 molar equivalents of bromine were added to 2-chloro-3-methyl thiophen (16g.) in CCl$_4$. The addition took about 3 hours and after completion, heating and illumination were continued for one-half hour. Analysis of the resulting products by nuclear magnetic resonance spectroscopy gave the following molar percentages of thiophen compounds:

| 2-chloro-3-methyl thiophen | 3% |
| 2-chloro-3-thenyl bromide | 2.5% |
| 2-chloro-3-thenylidine dibromide | 85% |

The solvent was removed under vacuum and the reaction mixture was hydrolysed with aqueous sodium carbonate solution. After steam distillation 11.9g. crude 2-chlorothiophen-3-aldehyde was obtained. This was 95% pure by nuclear magnetic resonance spectroscopy corresponding to 67% molar yield. Distillation gave 7.8g. of pure 2-chlorothiophen-3-aldehyde of melting point 25°C.

In similar manner satisfactory results are obtained when instead of starting with, and thus making, the described chloro-compounds, one uses the corresponding nitro, carboxylic, and trifluoromethyl compounds.

EXAMPLE 5

2,5-Dimethyl furan (10.4g.) and AZDN (0.5g.) were refluxed in carbon tetrachloride (150 ml.) and illuminated by means of a tungsten lamp. Bromine (10 ml. in 20 ml. carbon tetrachloride) was then slowly added. When 1.7 molar equivalents of bromine had been added the product isolated consisted of approximately equal parts of 2-bromomethyl-5-methyl furan and 2,5-di(bromomethyl) furan with no nuclear bromination detected.

EXAMPLE 6

3-Ethyl thiophen (20g.) and AZDn (0.5g.) in carbon tetrachloride (150 ml.) was heated to reflux and illuminated by means of a 150 watt tungsten spot-lamp. Bromine was slowly added as a 30% v/v solution in carbon tetrachloride. After one molar equivalent of bromine had been added the thiophens present were found to consist of 23% of 3-ethyl thiophen and 75% of 1-(3-thienyl)-1-bromo ethane.

EXAMPLE 7

2-Methyl benzo-[b]-thiophen (9g.) and AZDN (0.5g.) in 150 ml. carbon tetrachloride were heated under reflux in the presence of light from a tungsten lamp. One molar equivalent of bromine was added as a 30% solution in carbon tetrachloride to give a product containing benzothiophens in the proportions of 40% unchanged 2-methyl benzo-[b]-thiophen and 58% 2-bromomethyl benzo-[b]-thiophen.

EXAMPLE 8

In the experiment of Example 7 an additional 0.5g. AZDN was added and a further 2 molar equivalents of bromine. The aldehydes obtained on hydrolysis of the products consisted of approximately equal amounts of 2-formyl benzo-[b]-thiophen and 3-bromo-2-formyl benzo-[b]-thiophen.

EXAMPLE 9

2-Methyl thiophen-5-carboxylic acid was dissolved in carbon tetrachloride (150 ml.) and chloroform (10 ml.) and AZDN (0.5g.) was added. The mixture was refluxed over a 150 watt tungsten spotlight. Two molar equivalents of bromine as a 30% v/v solution in carbon tetrachloride were slowly added. A precipitate was formed but the mixture continued to take up bromine. After the addition of the two molar equivalents, solvent was boiled off until the volume was 100 ml. and the product treated with sodium carbonate solution with gentle heating for two hours to obtain 2-formyl thiophen-5-carboxylic acid in the form of a yellow solid after acidification, extraction and removal of the solvent.

EXAMPLE 10

3-Methyl thiophen (20g.) and AZDN (0.5g.) were refluxed in carbon tetrachloride (150 ml.) in a flask illuminated with a 100 watt ultra-violet lamp. Bromine as a 30% solution in the same solvent was slowly added. The addition of one molar equivalent gave a mixture of thiophens analysed by nuclear magnetic resonance spectroscopy as follows:

| | |
|---|---|
| 3-methyl thiophen | 30% |
| 2-bromo-3-methyl thiophen | 26% |
| 3-thenyl bromide | 22% |
| 3-thenylidine dibromide | 14% |

EXAMPLE 11

Following the procedure of Example 10 but adding a total of 2 molar equivalents of bromine, gave thiophens of the following analysis:

| | |
|---|---|
| 2-bromo-3-methyl thiophen | 35% |
| 2-bromo-3-thenyl bromide | 8% |
| 3-thenyl bromide | 27% |
| 3-thenylidine dibromide and 2-bromo-3-thenylidine dibromide | 30% |

EXAMPLE 12

3-Methyl thiophen (135 ml.) and AZDN (0.5g.) were refluxed in a flask heated and illuminated by a 150 watt tungsten spotlight. No additional solvent was used and the temperature was maintained at 80°C by reducing the pressure in the system. Bromine (15 ml.) was added slowly. Analysis of the products by nuclear magnetic resonance spectroscopy showed that they contained

| | |
|---|---|
| 3-methyl thiophen | 77% |
| 3-thenyl bromide | 10% |
| nuclear brominated methyl thiophens | 13% |

EXAMPLE 13

2,5-Dibromo-3-methyl thiophen (43 g.) in 150 ml. carbon tetrachloride with 0.5 g. AZDN were refluxed over a tungsten lamp and 2 molar equivalents of bromine as a 25% solution in carbon tetrachloride were added slowly. On the completion of the addition, the reaction mixture was stirred overnight with sodium carbonate solution, separated, dried and evaporated down to give 71.2 g. of a red liquid. This was shown to be 80% 2,5-dibromo-3-(dibromomethyl thiophen) by nuclear magnetic resonance spectroscopy. This material was stable both thermally and to hydrolysis and could be distilled at high vacuum as a colourless liquid.

EXAMPLE 14

2-Methyl thiophen (20 g.) and AZDN (0.5 g.) in 150 ml. carbon tetrachloride were heated under reflux and illuminated by means of a 150 watt tungsten lamp. Bromine (3 mole equivalents) was added as a 25% solution in carbon tetrachloride. On alkaline hydrolysis and subsequent acidification the aqueous phase yielded 4 g. of 2-bromothiophen-5-carboxylic acid indicating a 9% yield of 2-bromo-5-tribromomethyl thiophen in the reaction mixture.

The fact that the use of bromine is essential if solely ring substitution is to be avoided is demonstrated by the following comparative Example.

EXAMPLE 15

3-Methyl thiophen (20 g.) and AZDN (0.5 g.) in carbon tetrachloride (150 ml.) were held at reflux over a 150 watt tungsten spot-lamp. Chlorine was passed into the solution and the reaction products were analysed at intervals. It was found that chlorination occurred solely in the ring giving 2,5-dichloro-3-methyl thiophen together with addition compounds.

What we claim is:

1. A process of making a compound of Formula 1

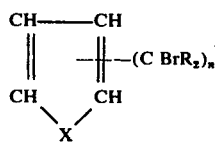   1 from a compound of Formula 2

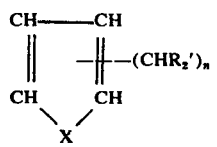   2 in which $n$ is 1 or 2, X is oxygen or sulphur, the radicals R and R' may be the same or different and are Br, hydrogen or an aliphatic or aromatic group, and in which each ring may contain additional substituents provided that at least one CH group is unsubstituted, the process comprising gradually adding bromine to an organic liquid phase containing the compound of Formula 2 and reacting the bromine with the compound in the organic liquid phase in the presence of a radical initiator and illumination by visible or ultra violet light, the rate of addition of bromine being such that the liquid phase substantially never acquires a red brown colour.

2. A process according to claim 1 in which the reaction is conducted under reflux.

3. A process according to claim 1 in which the reaction is conducted under reflux under atmospheric pressure.

4. A process according to claim 1 in which the reaction is conducted at a temperature of 70° to 110°C.

5. A process according to claim 1 in which the organic liquid phase comprises an inert solvent.

6. A process according to claim 1 in which the organic liquid phase comprises an inert solvent selected from carbon tetrachloride, chloroform and benzene.

7. A process according to claim 1 in which the ring contains at least one substituent selected from nitro, carboxylic, bromo, chloro, trifluoro-methyl and alkyl.

8. A process according to claim 1 in which adjacent positions on the ring in the compounds of Formulae 1 and 2 are substituted by a fused ring.

9. A process according to claim 1 in which the compounds are benzo thiophens.

10. A process according to claim 1 in which any aliphatic group R or R' is alkyl and any aromatic group R or R' is a phenyl group.

11. A process according to claim 1 in which $CHR_2'$ represents alkyl.

12. A process according to claim 1 in which $CHR_2'$ is methyl or ethyl.

13. A process according to claim 1 in which $n$ is 1.

14. A process according to claim 1 in which X is sulphur.

15. A process according to claim 1 in which not more than one radical R is bromine.

16. A process according to claim 1 in which sufficient bromine is added that only one radical R is Br.

17. A compound of Formula 1 made by a process according to claim 1.

* * * * *

UNITED STATES PATENT OFFICE
CERTIFICATE OF CORRECTION

PATENT NO. : 3,947,336
DATED : March 30, 1976
INVENTOR(S) : James A. Clarke et al It is certified that error appears in the above-identified patent and that said Letters Patent are hereby corrected as shown below:

at Col. 5, lines 38 & 39, the following sentence was added to the original patent, but does not appear in the application. Omit "In particular the mixture substantially never exceeded orange".

Signed and Sealed this

Tenth Day of August 1976

[SEAL]

Attest:

RUTH C. MASON
Attesting Officer

C. MARSHALL DANN
Commissioner of Patents and Trademarks